United States Patent [19]

Thomas et al.

[11] Patent Number: 6,150,392
[45] Date of Patent: Nov. 21, 2000

[54] EFFECTIVE METHOD FOR THE AMELIORATION AND PREVENTION OF TISSUE AND CELLULAR DAMAGE

[76] Inventors: Peter G. Thomas, 14 Old Farm Rd., Charlottesville, Va. 22903; Jose-Luis Diaz, 112 Wenonah Way, Durham, N.C. 27713

[21] Appl. No.: 09/220,360

[22] Filed: Dec. 24, 1998

Related U.S. Application Data

[63] Continuation of application No. 08/834,121, Apr. 14, 1997, Pat. No. 5,854,271, which is a continuation of application No. 08/235,950, May 2, 1994, abandoned.

[51] Int. Cl.⁷ .................................................. A61K 31/415
[52] U.S. Cl. ............................................................... 514/400
[58] Field of Search .............................................. 514/400

[56] References Cited

U.S. PATENT DOCUMENTS

| | | | |
|---|---|---|---|
| 5,280,038 | 1/1994 | Kukreja et al. | 514/400 |
| 5,336,616 | 8/1994 | Livesey et al. | 435/240.2 |
| 5,352,691 | 10/1994 | Thomas | 514/385 |

OTHER PUBLICATIONS

Nathan et al, Biological Abstracts, vol. 76, No. 10, abstract No. 73676, 1983.

*Primary Examiner*—William R. A. Jarvis
*Attorney, Agent, or Firm*—Isaac Angres; Susan Petraglia

[57] ABSTRACT

The administration of histidine is able to prevent and ameliorate tissue and cellular damage which is caused by damaging levels of cytokines and growth factors. It is shown that histidine, when administered in therapeutic quantities is able to inhibit cytokines and growth factors involved in cell and tissue damage. In addition, the method of adminstering histidine to inhibit these molecules can prevent and ameliorate tissue, vessel and cell damage from restenosis, burns, surgical procedures and other disorders which cause and result from damaged tissues, vessels and cells.

1 Claim, No Drawings

EFFECTIVE METHOD FOR THE AMELIORATION AND PREVENTION OF TISSUE AND CELLULAR DAMAGE

This application is a continuation of Ser. No. 08/834,121, Apr. 14, 1997, now U.S. Pat. No. 5,854,271 which is a continuation of Ser. No. 08/235,950, filed May 2, 1994 now abandoned.

BACKGROUND OF THE INVENTION

1. Field of the Invention

The present invention generally relates to a method for reducing and preventing cell and tissue damage. More particularly, the present invention is directed to the administration of L-histidine, an amino acid, for the prevention, control, and amelioration of tissue, vessel and cell damage from cytokines and related molecules.

2. Description of the Prior Art

Cytokines are a general class of peptide or glycoprotein molecules which are involved in cell-to-cell signaling and interaction. In particular, these molecules are involved in a variety of immune system and inflammatory responses. The cytokines are numerous and include at least lymphokines, monokines, tumor necrosis factor (TNF), colony stimulating factors (CSFs), growth factors, and interleukins. A number of the cytokines are involved in the stimulation of growth, differentiation and other functions in a variety of target cells. It should be understood that the term cytokine is being used to describe the general group of modulators involved in intercellular interaction and signaling. This term is not intended to be limiting and can include any number of molecules which are involved in these systems, as would be understood by one of ordinary skill in the art.

In contrast to hormones, which are usually continuously produced by discrete glands, cytokines are generally produced after stimulation by virtually every cell type. In addition, a particular cell type can produce a variety of different cytokines.

A number of cytokines have been identified and cloned, however, at present, unique biologic activities can not be determined for most cytokines since nearly all types of cells have multiple receptors for and can respond to a variety of cytokines. In addition, it is thought that there is a considerable overlap in the biologic activities of cytokines. Furthermore, it has been shown that there is a redundancy of action among cytokines.

The characteristics, described supra, enable cellular responses to utilize alternative pathways and allow suboptimal concentrations of cytokines to cooperate in inducing the responses. Cytokines are also able to amplify the response by inducing the production of other cytokines leading to cascades and networks of interacting cytokines.

It is known that some cytokines are involved in the up and down regulation of immune and inflammatory leukocytes, and in regulation of activity in connective tissue and neural, epithelial, endothelial, and other cell types which are involved in tissue repair and restoration of homeostasis.

In general, normal levels of cytokines are benign in their effects on tissues and cells. However, the overproduction of cytokines can have harmful effects on tissues and can result in cellular damage, capillary leakage and even death. In addition, cytokines have been implicated in neointimal hyperplasia or cell proliferation following surgical procedures, cancer, allergy, infection, angiogenesis, and restenosis. At present, it is thought that TNF and interleukin-1 (IL-1) are particularly involved in producing some of these harmful effects. However, it is anticipated that other cytokines present in excessive amounts will result in cellular and tissue damage.

At present, cytokine-mediated cellular damage is generally treated through the administration of drugs such as vaccines, antiviral compounds, antibiotics, antibodies, receptor-site blockers, antisense nucleotides, and anti-adhesion compounds. These drugs have all been designed to target or act on (i.e. block) specific receptor sites on cells.

However, it is important to note that since the cytokines play an important role in normal defense against infection, it is necessary to maintain the ability of the cells to produce adequate amounts of cytokines to prevent infection.

It has been shown by experimental data, set forth in Libby et al. Cascade Model for Restenosis, Circulation, Supplement III, 86:III-47 to III-52 (1992) that a cytokine/growth factor mechanism is involved in the initiation and proliferation of restenosis. It was found that vessel injury induces cytokine expression and causes a continuing growth factor and cytokine cascade which can account for the defective smooth muscle function observed in restenosis. Therefore, it is suggested that control of the cytokine and growth factor levels could prevent damage caused by restenosis.

Furthermore, experimental data has shown that burn and wound injuries can result in damaging levels of cytokines and growth factors and therefore can result in tissue and cell damage. As discussed by J. S. Solomrkin, M. D. in *Neutrophil Disorders in Burn Injury: Complement, Cytokines and Organ Injury, J.* of Trauma, Vol. 30, No. 12, Supplement, S80–S85, burn injury can induce a cascade of cytokines and growth factors which can cause an inflammatory response which can result in tissue and cellular injury and loss. It is also known that this response occurs with other wound and surgical injuries. In addition, it has been suggested that calpain is involved in the inflammatory response. Therefore, a reduction in the production of these factors will reduce the amount of tissue and cellular damage induced by burn, wound and surgical injury.

The drugs developed to date block the production of cytokines and may interfere with the host defense mechanisms, thereby subjecting individuals to an increased risk of infection. In addition, the drugs currently in use do not reduce the broad-spectrum of tissue damage caused by cytokines and other chemotactic factors.

SUMMARY OF THE INVENTION

It is therefore an object of the present invention to provide a method of using histidine to decrease the production of certain cytokines.

It is another object of this invention to provide a method of using histidine to prevent, control or ameliorate tissue and cell damage from cytokines and growth factors.

It is a further object of this invention to provide a method which does not interfere with host defense mechanisms.

It is another object of this invention to provide a method of administering histidine to prevent or treat damage caused by restenosis.

It is also an object of the present invention to provide a method of using histidine to prevent, control or ameliorate tissue and cell damage after burn, wound or surgical injuries.

According to the invention, experiments have been conducted which demonstrate that histidine is effective in reducing elevated levels of cytokines and growth factors. Therefore, histidine is able to protect against tissue and cell damage from these molecules while enabling the host to maintain its normal defense mechanisms.

DETAILED DESCRIPTION OF THE PREFERRED EMBODIMENTS OF THE INVENTION

It has been discovered that the amino acid histidine is beneficial in the reduction of the cytokines and growth factors and in particular the prevention and amelioration of tissue and cell damage which is caused by an overabundance of these molecules. The excessive production or release of cytokines and growth factors can lead to a variety of conditions, including restenosis. Therefore, the administration of histidine, which inhibits the quantities of cell and tissue-damaging cytokines and growth factors, can be effective in preventing or treating damage associated with restenosis. In the following discussion it is understood that the term "patients" as used herein shall mean animals, as well as humans.

In vitro studies demonstrated the beneficial effects of histidine on the inhibition of damaging cytokines and growth factors. In these experiments, human macrophages, which when activated release cytokines, were exposed to a variety of compounds which are known to stimulate a response in macrophages. These stimulants included lipopolysaccharide (LPS), zymosan, f-MET-LEU-PHE and TNF-a. Each of these stimulants has been found to stimulate the production of chemotactic cytokines and growth factors at levels which are sufficient to result in tissue and cellular damage. The macrophages were incubated in concentrations and for a period of time which is known to stimulate human peripheral monocytes and induce the production of cytokines and growth factors. The details for each stimulant are set forth in Table 1.

|   | Histidine | Inhibition Concentration 50 | Comments | Stimulants |
|---|---|---|---|---|
| TNF-a | inhibition | IC50 ≈ 25 mM | inhibition only at first dilution. | Lipopoly-saccharide (LPS) 100 ng/ml, incubate 16 hours. |
| IL-1B | inhibition | IC45 ≈ 50 mM | inhibition only at first dilution. | LPS 100 ng/ml, incubate 16 hours. |
| IL-6 | stimulation | EC50 ≈ 10 mM (EC = effective stimulation) | (+LPS) | LPS 100 ng/ml, incubate 16 hours. |
| IL-8 | stimulation | EC50 < 50 mM | (+LPS) very high background levels of IL-8 | LPS 100 ng/ml, incubate 16 hours. |
| IL-1ra | inhibition | IC50 ≈ 40 mM | inhibition only at first dilution. | Unstimulated |
| GM-CSF | inhibition | IC50 ≈ 25 mM | inhibition only at first dilution. | LPS 100 ng/ml, incubate 16 hours. |
| PDGF | no effect | | | LPS 100 ng/ml, incubate 16 hours. |
| TF | inhibition | IC45 ≈ 50 mM | inhibition only at first dilution. | LPS 100 ng/ml, incubate 16 hours. |
| LTB4 | no effect | | | ZYMOSAN 300 mg/ml, incubate 90 minutes. |
| PGE2 | no effect | | | ZYMOSAN 300 mg/ml, incubate 90 minutes. |
| PAF | inhibition | IC30 ≈ 50 mM | inhibition only at first dilution. | ZYMOSAN 300 mg/ml, incubate 90 minutes. |
| OKT3 | inhibition | IC40 ≈ 50 mM | inhibition only at first dilution. | |
| PHA | inhibition | IC50 ≈ 25 mM | inhibition only at first dilution. | |
| MLR | inhibition | IC50 ≈ 25 mM | inhibition only at first dilution. | |
| Chemotaxis | inhibition | IC50 ≈ 40 mM | inhibition only at first dilution. | f-MET-LEU-PHE 5 × 10 − 9 molar, incubate 90 minutes. |
| Adhesion | no effect | | | TNF-a 500 pg/ml, incubate 5 hours. |

The studies clearly demonstrate that L-histidine, when administered at appropriate concentrations, is effective in inhibiting tumor necrosis factor (TNF); interleukin-1 beta (IL-1B); interleukin-1 receptor antagonist (IL1-ra); granulocytemacrophage colony stimulating factor release (GM-CSF); procoagulant (tissue factor) (TF) function; platelet activating factor (PAF); proliferation functions, for example proliferation of lymphocytes including OKT-3 (CD-3), phytohemoagglutinin (PHA) stimulated proliferation, and mixed lymphocyte reaction (MLR); and monocyte chemotaxis. In addition, histidine was shown to have no effect on platelet derived growth factor (PDGF), prostaglandin (PGE$_2$), leukotriene (LTB$_4$), and adhesion. As shown, histidine is effective in control and preventing the proliferation of the cytokines which are involved in damaging tissues and cells. Therefore, histidine can be administered to reduce the quantities of cytokines and growth factors, thereby preventing and ameliorating the damaging effects of cytokines and growth factors.

It is known that in individuals with wounds or burns, or who have undergone surgery or suffered other injuries of tissue often have elevated levels of cytokines, growth factors and calpains.

It is anticipated that histidine, by reducing the damaging cytokines and growth factors to more normal levels, will help to restore the viability of tissue following an injury, as well as prevent damage to healthy tissue. In addition, it is believed that histidine can prevent and ameliorate damage to tissues and cells from ischemia and damage caused by medical or surgical procedures that are directed at the injured tissues.

A current investigation has been undertaken by the inventors using an ischemic hind limb model. An example of the protocol used for these studies is to first intravenously administer 100 mg/kg of L-histidine to Sprague Dawley rats.

This administration is approximately 45 minutes prior to ischemia. After the study, the level of calcium-activated neutral proteases (calpains) is assayed with immunological techniques using a standard tri-tetrazolium triphenyl chloride (TTC) stain and spectrophotometric measurements. The level of calpain is used to determine the survival of muscle tissue.

As discussed supra, histidine's ability to reduce the levels of damaging cytokines and growth factors will increase the rate of survival of tissues and cells since the damage to cells and tissues is a direct consequence of the elevated levels of cytokines and growth factors.

It has been demonstrated that during interventional and surgical procedures, both healthy and diseased tissue are injured. In particular, studies, discussed supra, have shown that a cytokine growth factor cascade may be involved in the amplification and proliferation process which results in restenosis. The administration of histidine can effectively prevent or ameliorate the cascade by inhibiting the cell-damaging cytokines and growth factors.

Currently investigations are continuing under the direction of the inventors. Some exemplary methods include the use of a rat carotid injury model. In this method, the left carotid artery of the rat is denuded of endothelium by passage of a distending Fogarty balloon catheter throughout its length. This procedure results in immediate formation of a platelet monolayer, medial smooth muscle cell proliferation beginning within 24 hours with subsequent cellular migration into the intima, and development of a concentric fibromuscular neointimal layer by 2 weeks.

There are 50 rats with equal numbers divided into the following test groups: a control group, with the balloon injury only; an intraluminal control group, with a balloon injury and the intraluminal administration of buffer; an intraluminal active therapy group, with a balloon injury and intraluminal administration of L-histidine in a buffer solution; a pluronics control group, with a balloon injury and periadventitial pluronics coating; and a pluronics active therapy group, with balloon injury and periadventitial L-histidine in pluronics coating.

The animals are sacrificed approximately two weeks after balloon injury and drug therapy, and then the carotid vessels perfusion-fixed, and quantitative morphometric analysis is performed to assess the extent of neointimal thickening in each of the five treatment groups.

It is anticipated that the inhibition of cytokines and growth factors through the administration of histidine will inhibit undesired or abnormal cell and tissue growth since the abnormal growth and proliferation of cells and tissues is directly in response to these molecules.

While the invention has been described in terms of its preferred embodiments, those skilled in the art will recognize that the invention can be practiced with modification within the spirit and scope of the appended claims.

We claim:

1. A method of preventing proliferation of or reducing levels of tissue-damaging cytokines or growth factors in a mammal in need thereof comprising the step of providing to said mammal an effective amount of histidine to prevent proliferation or reduce levels of said cytokines or growth factors.

* * * * *